US009517565B2

(12) United States Patent
Song et al.

(10) Patent No.: US 9,517,565 B2
(45) Date of Patent: Dec. 13, 2016

(54) FEEDING ASSISTANT ROBOT

(71) Applicant: National Rehabilitation Center, Seoul (KR)

(72) Inventors: Won Kyung Song, Seoul (KR); Jong Bae Kim, Seoul (KR); Kwang Ok An, Incheon (KR); In Ho Lee, Seoul (KR); Won Jin Song, Gyeongsangnam-Do (KR)

(73) Assignee: NATIONAL REHABILITATION CENTER, Seoul (KR)

( * ) Notice: Subject to any disclaimer, the term of this patent is extended or adjusted under 35 U.S.C. 154(b) by 52 days.

(21) Appl. No.: 14/732,434

(22) Filed: Jun. 5, 2015

(65) Prior Publication Data
US 2015/0375397 A1 Dec. 31, 2015

Related U.S. Application Data

(62) Division of application No. 13/639,754, filed as application No. PCT/KR2010/009325 on Dec. 24, 2010, now Pat. No. 9,066,615.

(30) Foreign Application Priority Data

Apr. 7, 2010 (KR) .................. 10-2010-0031948

(51) Int. Cl.
*B25J 9/16* (2006.01)
*B25J 11/00* (2006.01)
(Continued)

(52) U.S. Cl.
CPC .............. *B25J 11/009* (2013.01); *A47G 21/08* (2013.01); *A61F 4/00* (2013.01); *B25J 9/0084* (2013.01);
(Continued)

(58) Field of Classification Search
CPC .. A47G 21/08; A61F 4/00; A63F 2003/00908; B25J 11/008; B25J 15/0206; B25J 9/0084; B25J 9/0096; B25J 9/04; G05B 2219/45111
(Continued)

(56) References Cited

U.S. PATENT DOCUMENTS 3,907,126 A 9/1975 Sydnor, Sr.
4,398,720 A * 8/1983 Jones ................. A63F 3/00643
273/238
(Continued)

FOREIGN PATENT DOCUMENTS

JP 2003-062019 A 3/2003
JP 2004-008327 A 1/2004
(Continued)

*Primary Examiner* — Gregory Adams
(74) *Attorney, Agent, or Firm* — Rabin & Berdo, P.C.

(57) ABSTRACT

The present invention relates to a feeding assistant robot, which assists in feeding patients or the elderly and infirm who have difficulty in moving their arms and thus have difficulty in feeding themselves. The feeding assistant robot includes: a picking arm including a gripper for picking up food placed on a tray; a feeding arm, including a spoon on which the food picked up by the picking arm is placed, for moving the spoon to the mouth of a user; an input device enabling the user to direct the movements of the picking arm and of the feeding arm; and a control unit electrically connected to the picking arm, the feeding arm, and the manipulation part to control the movements of the picking arm and the feeding arm according to the commands from the input device.

8 Claims, 12 Drawing Sheets

(51) Int. Cl.
*B25J 15/02* (2006.01)
*B25J 13/02* (2006.01)
*B25J 9/00* (2006.01)
*A47G 21/08* (2006.01)
*A61F 4/00* (2006.01)
*B25J 19/02* (2006.01)
*B25J 13/06* (2006.01)
*B25J 9/02* (2006.01)

(52) U.S. Cl.
CPC ............ *B25J 9/0096* (2013.01); *B25J 9/1664* (2013.01); *B25J 9/1679* (2013.01); *B25J 9/1682* (2013.01); *B25J 11/008* (2013.01); *B25J 13/02* (2013.01); *B25J 13/06* (2013.01); *B25J 15/0206* (2013.01); *B25J 19/02* (2013.01); *B25J 9/023* (2013.01); *G05B 2219/40521* (2013.01); *G05B 2219/45111* (2013.01)

(58) Field of Classification Search
USPC . 340/825.19; 414/1, 2, 4, 7, 706, 9; 604/57; 606/130; 623/65; 901/16, 8
See application file for complete search history.

(56) References Cited

U.S. PATENT DOCUMENTS

| | | | |
|---|---|---|---|
| 4,412,293 A | | 10/1983 | Kelley et al. |
| 5,056,964 A | | 10/1991 | Naka et al. |
| 5,197,846 A | * | 3/1993 | Uno .................. B25J 9/04 |
| | | | 414/731 |
| 5,241,249 A | * | 8/1993 | Detriche ............ B25J 9/1664 |
| | | | 318/568.11 |
| 5,497,674 A | | 3/1996 | Inada |
| 6,208,104 B1 | | 3/2001 | Onoue et al. |
| 6,471,504 B1 | | 10/2002 | Matsui |
| 8,240,967 B2 | * | 8/2012 | Guglielmelli ......... A47G 21/08 |
| | | | 414/9 |
| 9,066,615 B2 | * | 6/2015 | Song ................ B25J 11/008 |
| 2009/0104004 A1 | | 4/2009 | Guglielmelli et al. |

FOREIGN PATENT DOCUMENTS

| | | | |
|---|---|---|---|
| JP | 2004-081567 A | | 3/2004 |
| JP | 2006-000428 A | | 1/2006 |
| JP | 2006000428 A | * | 1/2006 |
| JP | 2008-238338 A | | 10/2008 |
| JP | 2008238338 A | * | 10/2008 |

* cited by examiner

FEEDING ASSISTANT ROBOT

CROSS-REFERENCE TO RELATED APPLICATIONS

This is a divisional application of U.S. application Ser. No. 13/639,754, filed Oct. 5, 2012. Furthermore, this application claims priority to Korean Application No. 10-2010-0031948, filed Apr. 7, 2010. The disclosure of these U.S. and Korean applications is incorporated herein by reference.

TECHNICAL FIELD

The present invention relates, in general, to feeding assistant robots and, more particularly, to a feeding assistant robot which assists in feeding a patient or the elderly and infirm who cannot easily move his/her arms to have a meal.

BACKGROUND ART

Different kinds of devices and robots for assisting in feeding patients or the elderly and infirm have come onto the market, and a lot of researches are in progress.

Particularly, a representative example of this technology was proposed in US Patent No. US2009/0104004, entitled "Self-feeding apparatus", which was applied on May 26, 2006 and published last year. As shown in FIG. 1, this conventional technique includes a support base, a food container, a spoon which is used to scoop food, and a mechanical unit which transfers the spoon to the mount of a user. This apparatus is configured such that the position of the spoon can be adjusted depending on the location of the mouth of the user. According to an input signal of the user, the apparatus repeats the operation of scooping food placed on a plate using the spoon and transferring it to a position adjacent to the mouth of the user.

However, in this apparatus, if food includes steamed rice which is sticky and a variety of side dishes, it is difficult to handle the food only using the operation of scooping it from the plate. Despite needs of the user such as a patient to have different kinds of foods, the user must have food contained on only the single plate.

DISCLOSURE

Technical Problem

Accordingly, the present invention has been made keeping in mind the above problems occurring in the prior art, and an object of the present invention is to provide a feeding assistant apparatus which makes it possible for a user to have a broad variety of foods contained in a typical food tray, and is configured such that the user can easily have food regardless of the kind of food.

In other words, the present invention aims to propose a system which assists in feeding a person who cannot easily move his/her arms attributable to spinal cord injuries, cerebral palsy, muscular disease, aging, etc., so that it is difficult for him/her to have Korean food, such as steamed rice which is sticky, or side dishes, placed on a table, by himself/herself, thereby making it possible for the user to have a desired kind of food whenever he/she wants, thus helping the user be independent and improving the quality of life.

Technical Solution

In order to accomplish the above object, the present invention provides a feeding assistant robot, including: a picking arm 100 provided with a gripper 110 picking up food placed on a food tray 10; a feeding arm 200 provided with a spoon 210 onto which the food picked up by the picking arm 100 is placed, the feeding arm 200 transferring the spoon 210 to a mouth of a user; an input device 300 enabling the user to instruct the picking arm 100 and the feeding arm 200 to be operated; and a control unit (not shown) electrically connected to the picking arm 100, the feeding arm 200, and the input device 300, the control unit controlling the operation of the picking arm 100 and the feeding arm 200 on the instruction of the input device.

The picking arm 100 may include: a first link 121 axially rotated by a motor that is provided in an axial direction; a second link 122 hinged to an end of the first link 121, the second link 122 being swung upward or downward by rotation of a motor; and a third link 123 hinged to an end of the second link 122, the third link 123 being swung upward or downward by rotation of a motor, wherein the gripper 110 is provided on an end of the third link 123.

The gripper 110 may be connected to the third link 123 by a universal joint 124 so that the gripper 110 is biased downward by gravity.

The gripper 110 may be hinged to the third link 123 so that the gripper 110 is able to be swung upward or downward by rotation of a motor.

The picking arm 100 may include a first link 131 connected at a first end thereof to a motor so that the first link 131 horizontally rotates around a rotating shaft, wherein the gripper 110 is provided on a second end of the first link 131 so as to be vertically movable.

The picking arm 100 may include a second link 132 hinged to a second end of the first link 131 so that the second link 132 is horizontally rotated by rotation of a motor, wherein the gripper 110 is provided on an end of the second link 132 so as to be vertically movable.

The gripper 110 may be connected to the second link 132 by a prismatic joint 133 so as to be vertically movable.

The feeding arm 200 may include: a first link 221 connected at a first end thereof to a motor so that the first link 221 is able to vertically swing around a rotating shaft; and a second link 222 rotatably connected to a second end of the first link 221 by a hinge, the hinge being connected to the motor provided on the first link 221 by a belt 223 so that the second link 222 is able to vertically swing in conjunction with the first link 221, wherein the spoon 210 is provided on an end of the second link 222 and oriented horizontally with the second link 222.

The feeding arm 200 may include: a first link 231 connected at a first end thereof to a motor so that the first link 231 is able to vertically swing around a rotating shaft; and a second link 232 hinged to a second end of the first link 231, the second link 232 being able to be vertically swung by rotation of a motor, wherein the spoon 210 is provided on an end of the second link 232 and oriented horizontally with the second link 232.

The feeding arm 200 may include: a first link 241 connected at a first end thereof to a motor so that the first link 241 is able to vertically swing around a rotating shaft; and a second link 242 hinged to a second end of the first link 241, the second link 242 being able to be vertically swung by rotation of a motor, wherein the spoon 210 is hinged to an end of the second link 242 and is able to be vertically swung by rotation of a motor.

The feeding arm 200 may include: a first link 251 connected at a first end thereof to a motor so that the first link 251 is able to vertically swing around a rotating shaft; and a second link 252 hinged to a second end of the first link 251, the second link 252 being able to be vertically swung by rotation of a motor, wherein the spoon 210 is connected to an end of the second link 242 by a prismatic joint 133 so as to be horizontally movable.

The gripper 110 may be connected to and rotated by a motor that is axially provided.

A sensing means 500 may be provided on at least either the picking arm 100 or the feeding arm 200.

Furthermore, a size and structure of the food tray 10 may be previously input in the control unit (not shown), and when the user designates food disposed at a predetermined position using the input device 300, the picking arm 100 may automatically move to the corresponding food, the gripper 110 may pick up the food and places the food on the spoon 210 of the feeding arm 200, and then the feeding arm 200 may move the spoon 210 to the mouth of the user.

When the user designates food disposed at a predetermined position using the input device 300, the control unit (not shown) may instruct the gripper 110 of the picking arm 100 to be immersed in a water bottle and pulled out of the water bottle before the gripper 110 picks up the food.

Each of food sections 11 of the food tray 10 may be partitioned into a plurality of areas depending on a size of the gripper 110, wherein the gripper 110 may pick up pieces of food in the food section in a preset sequence.

The designating the food using the input device 300 may comprise designating a plurality pieces of food.

The picking arm 100 and the feeding arm 200 may be provided in a single frame 600.

The picking arm 100 and the feeding arm 200 may move along rails (not shown) provided on the frame 600 so as to be adjustable in relative positions therebetween.

Advantageous Effects

A feeding assistant apparatus according to the present invention makes it possible a user who cannot easily move his/her arms to have food selected from among different kinds of foods whenever he/she wants. Furthermore, the feeding assistant apparatus of the present invention includes two robot arms so that it can effectively handle steamed rice which is sticky, and it can be easily applied to a variety of foods. Particularly, the present invention can be easily applied to Korean food which is centered on steamed rice. Thereby, the user can have a meal by himself/herself, facing his/her family.

Furthermore, because the present invention uses the two robot arms, it can be easily adapted to the Korean diet which must use chopsticks and a spoon. In addition, according to the present invention, steamed rice and side dishes are placed on a single spoon together so that the user can have them together in a single spooning movement. Further, for example, while one robot arm approaches the mouth of the user and then returns to its original position, the other robot arm can pick up food. As such, the two robot arms are intimately operated and thus are able to reduce the time for picking up food and transferring it to the user.

Moreover, the present invention can conduct the operation similar to that of a care worker who scoops steamed rice using a spoon and places food from side dishes on it. Furthermore, the present invention can be effectively used regardless of the style of the user that separately has steamed rice and side dishes or has steamed rice and side dishes together during a single spooning movement.

BEST MODE

Hereinafter, preferred embodiments of the present invention will be described in detail with reference to the attached drawings. The terms and words used in the specification and claims must not be limited to typical or dictionary meanings, but must be regarded as concepts selected by the inventor as concepts which best illustrate the present invention, and must be interpreted as having meanings and concepts adapted to the scope and spirit of the present invention to aid in understanding the technology of the present invention.

Therefore, the construction of the embodiment illustrated in the specification and the drawings must be regarded as only one illustrative example, and these are not intended to limit the present invention. Furthermore, it must be understood that various modifications, additions, and substitutions are possible at the point of time of application of the present invention.

Figure 1:
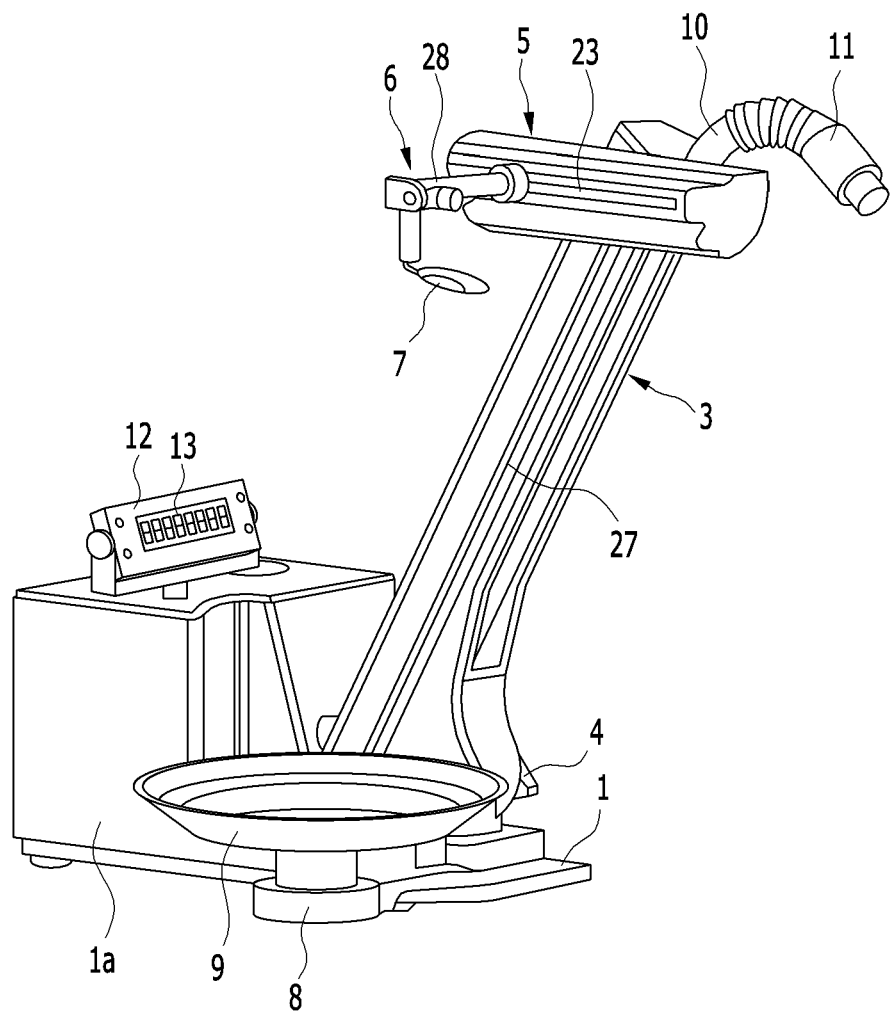
FIG. 1 is a perspective view showing a conventional technique.
Figure 2:
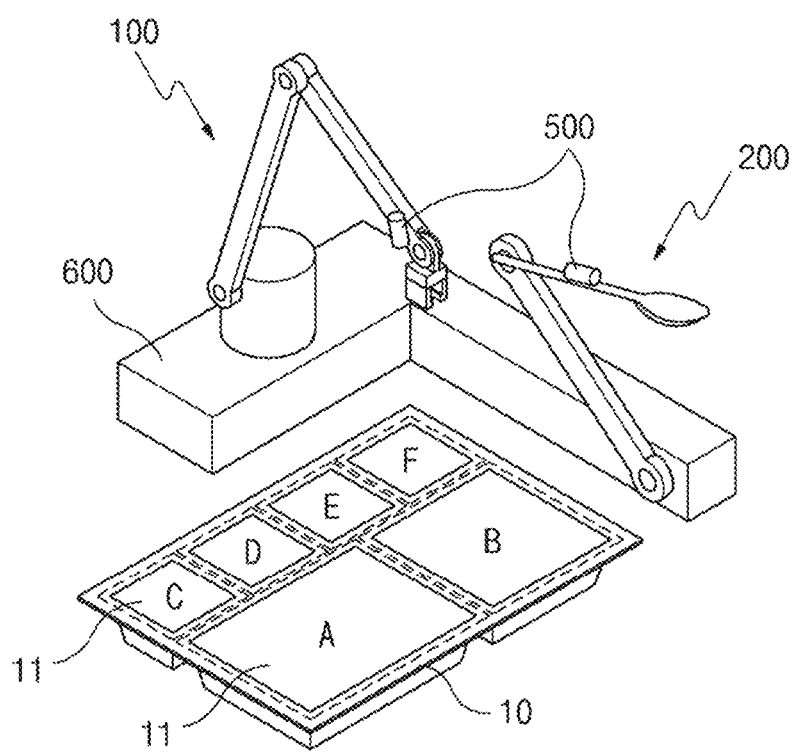
FIG. 2 is a view illustrating the general construction of the present invention.
Figure 11:
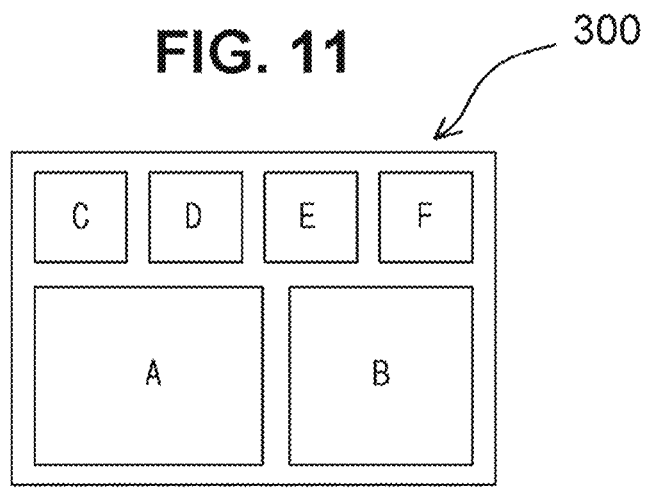
FIGS. 11 and 12 illustrate embodiments of an input device which is one of the elements constituting the present invention.
Figure 12:
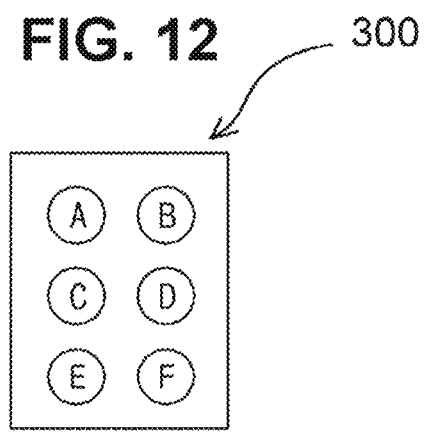
Figure 13:
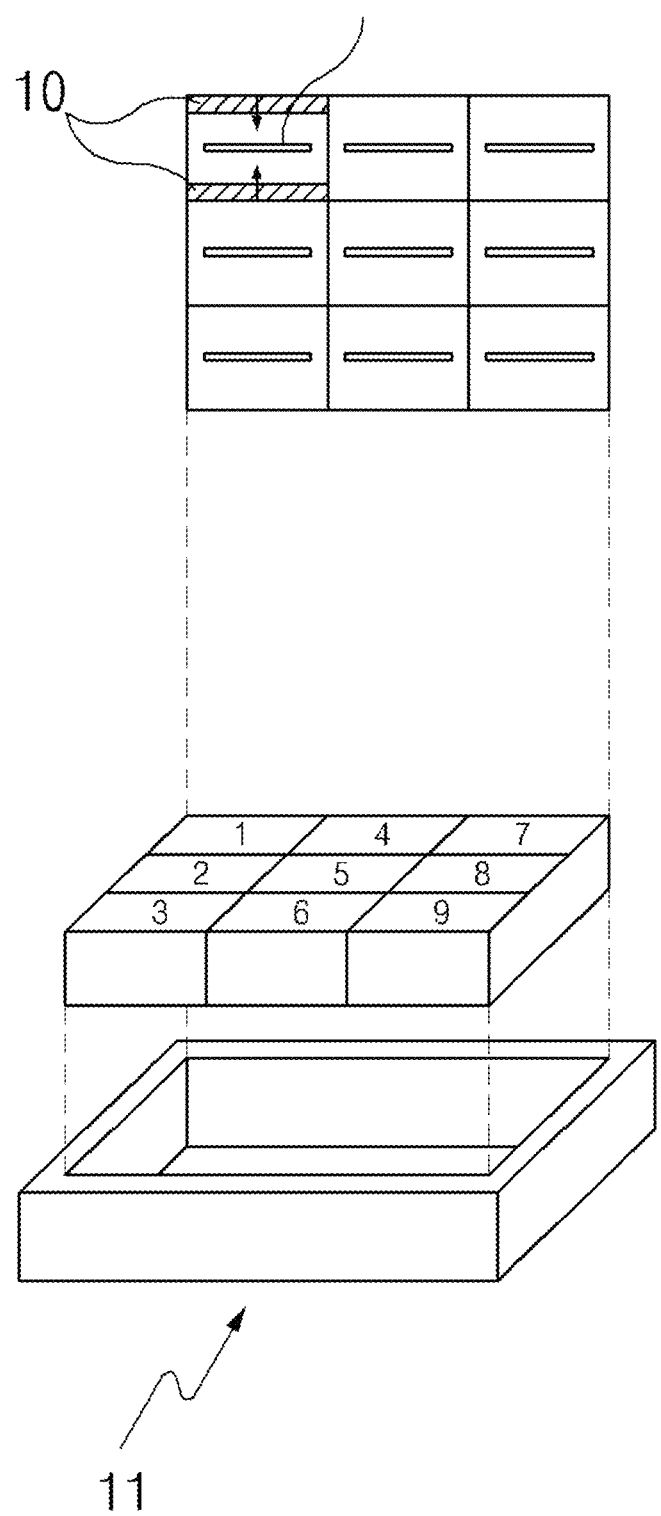
FIGS. 13 through 15 are views showing embodiments of sections in which a gripper grips food and a sequence in which the gripper grips food in the sections according to the present invention.
Figure 14:
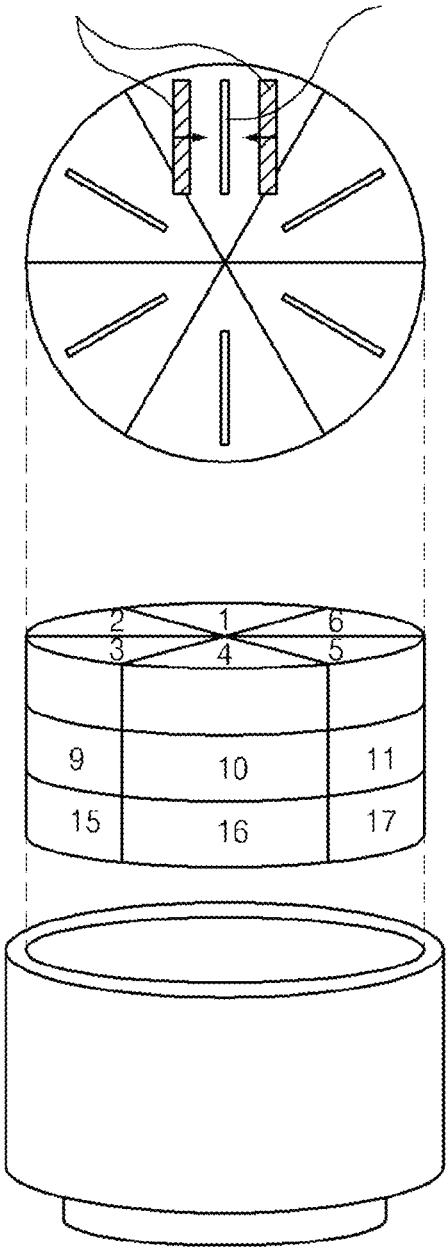
Figure 15:
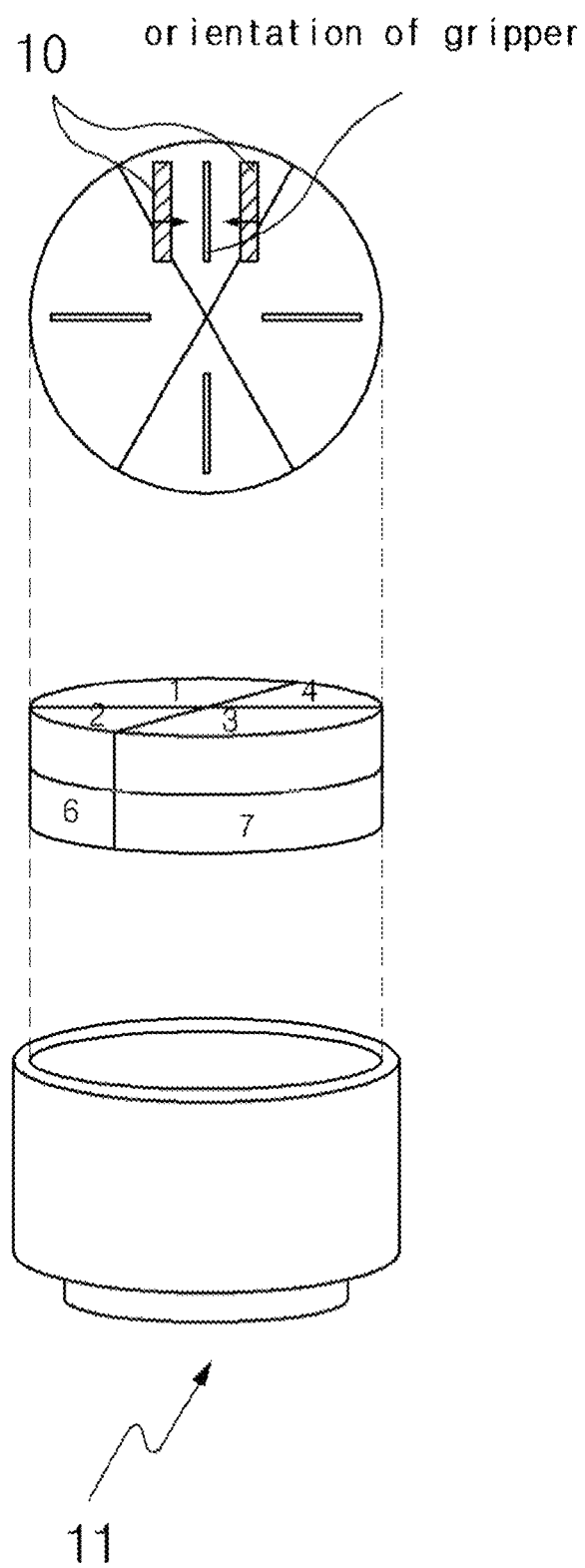

FIG. 2 is a view illustrating the general construction of the present invention. FIGS. 3 through 6 are views illustrating embodiments of a picking arm which is one of elements constituting the present invention. FIGS. 7 through 10 illustrate embodiments of a feeding arm which is one of the elements constituting the present invention. FIGS. 11 and 12 illustrate embodiments of an input device which is one of the elements constituting the present invention. FIGS. 13 through 15 are views showing embodiments of sections in which a gripper grips food and a sequence in which the gripper grips food in the sections according to the present invention.

As shown in FIG. 2, the feeding assistant robot according to the present invention includes the picking arm 100, the feeding arm 200, the input device 300, and a control unit (not shown). That is, the present invention is a system which assists a user in eating food which is contained in a food tray 10 on a table without using his/her arm.

In detail, the feeding assistant robot according to the present invention can be used after the food tray 10 that contains food has been placed on the table, for example, by another person. There is no limit for the kind or size of the food tray 10. A typical food tray can be used as the food tray 10. Moreover, general dishes, rice bowls, etc. can also be used so long as they can be provided with a fixing means.

Furthermore, food introduced in the present invention may be steamed rice and side dishes such as vegetables, centered on the Korean food menu. It is assumed that the food was previously prepared in bite size pieces. Furthermore, although steamed rice may be provided in a shape like sushi, it is assumed that steamed rice is contained in a bowl without having a special shape for the sake of convenience. These are just assumption, and the present invention is not limited to these. In other words, the present invention can be applied to other different kinds of foods.

The picking arm 100 is provided with the gripper 110 which grips food placed in the food tray 10, so that the picking arm 100 can grip food which is contained in a predetermined position of the food tray 10, without restriction. The gripper 110 is configured to have a clamp. Depending on a user, the size of the gripper 110 can be changed. It is preferable that the gripper 110 itself includes a device which can adjust the width of the clamp.

Food which is picked up by the gripper 110 is placed on a spoon 210 provided on the feeding arm 200 by the operation of the picking arm 100.

In the present invention, the picking arm 100 must have at least a triple-degree of freedom. In other words, the picking arm 100 must be able to move in front-rear, left-right and up-down directions to govern the entire area of the food tray 10 and easily pick up food that the user selects.

Figure 3:
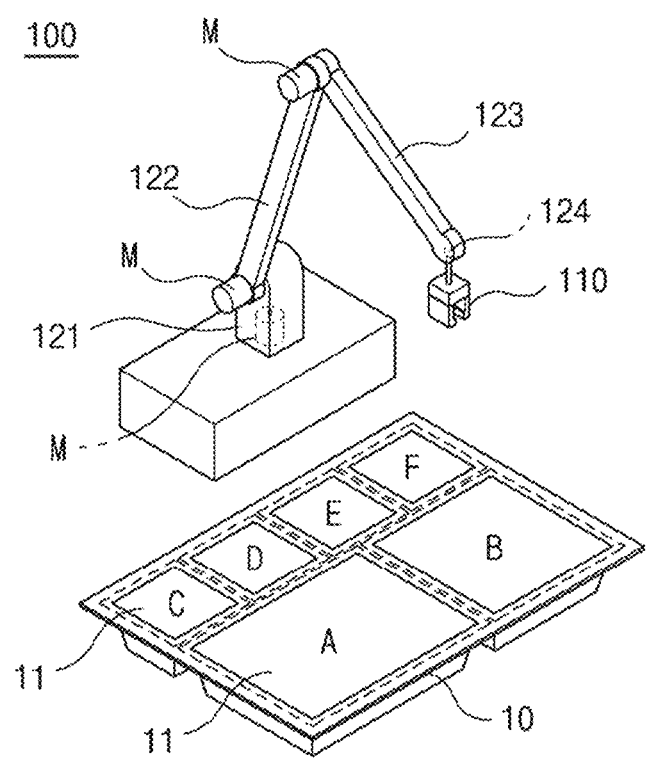
FIGS. 3 through 6 are views illustrating embodiments of a picking arm which is one of elements constituting the present invention.

As shown in FIG. 3, a first embodiment of the picking arm 100 includes: a first link 121 which is axially rotated by a motor that is provided in the axial direction; a second link 122 which is hinged to an end of the first link 121 and swung upward or downward relative to the first link 121 by rotation of a motor; and a third link 123 which is hinged to an end of the second link 122 and swung upward or downward relative to the second link 122 by rotation of a motor. The gripper 110 is provided on an end of the third link 123. Preferably, the gripper 110 is connected to the third link 123 by a universal joint 124 so that the gripper 110 is biased downward by gravity.

As such, the picking arm 100 has a general crane shape and is able to move upward and downward. Further, the first link 121 can axially rotate and thus horizontally move without restriction. Thereby, the gripper 110 can cover the entire area of the food tray 10.

Figure 4:
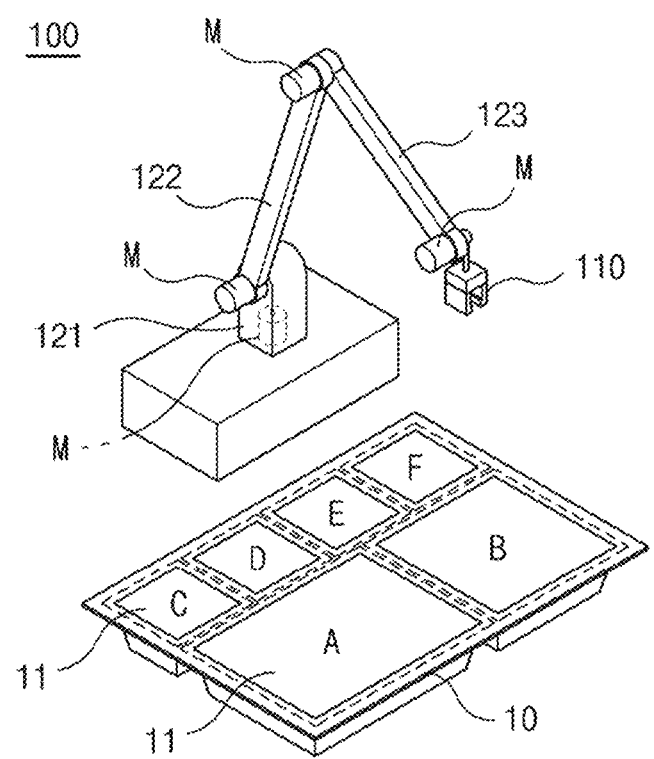

FIG. 4 illustrates a second embodiment of the picking arm 100. The general construction of the second embodiment of the picking arm 100, with the exception of a structure in which the gripper 110 is hinged to the third link 123 and swung relative to the third link 123 upward or downward by rotation of a motor, is the same as that of the first embodiment of the picking arm 100. The applicability of this embodiment can be further enhanced, because the gripper 110 can swing relative to the third link 123.

Figure 5:
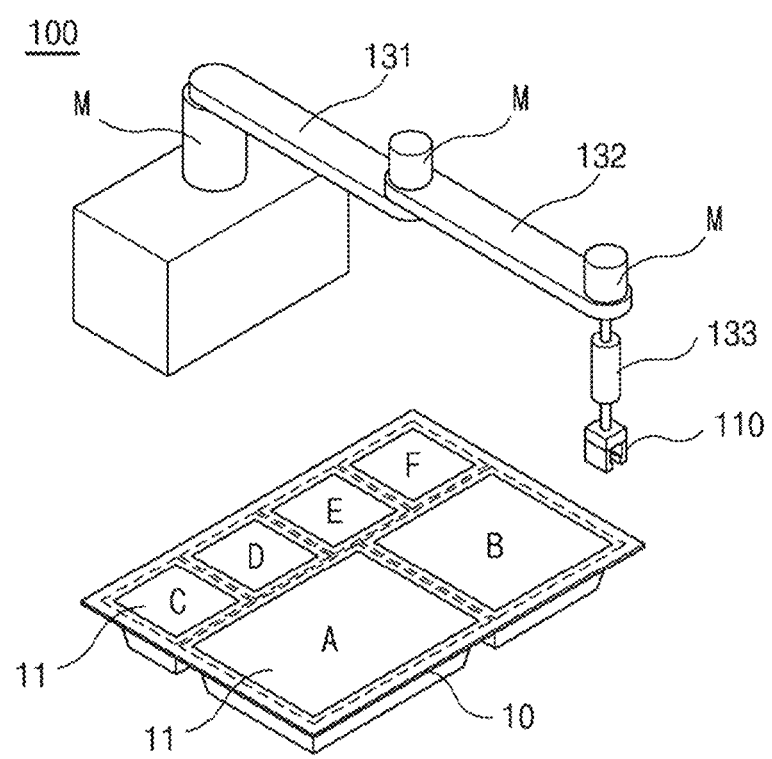

As shown in FIG. 5, a third embodiment of the picking arm 100 includes a first link 131 which is connected at a first end thereof to a motor and is horizontally rotated by the motor around a rotating shaft, and a second link 132 which is hinged to a second end of the first link 131 and is horizontally rotated relative to the first link 131 by rotation of a motor. A gripper 110 is provided on an end of the second link 132 so as to be vertically movable.

In this embodiment, the second link 132 and the gripper 110 are connected to each other by a prismatic joint 133 so that the gripper 110 can vertically move.

Furthermore, the apparatus of the third embodiment may be configured such that only the first link 131 is provided and the gripper 110 is provided on the second end of the first link 131 so as to be vertically movable. Although the functionality of this structure is reduced, the structure of the apparatus can be simplified and the production cost thereof can be reduced.

The third embodiment is basically configured such that the first and second links 131 and 132 are provided so as to be horizontally movable and the gripper 110 provided on the end of the second link 132 vertically moves and grips food. The vertical movement of the gripper 110 can be realized by the prismatic joint 133.

The prismatic joint 133 is a linear motion device, for example, including a ball screw and nut. In detail, rotation of a motor is transmitted to the ball screw by a gear unit, and thereby an element that is provided on the ball screw linearly moves.

In the present invention, all kinds of well known prismatic joints can be used without restriction.

Figure 6:
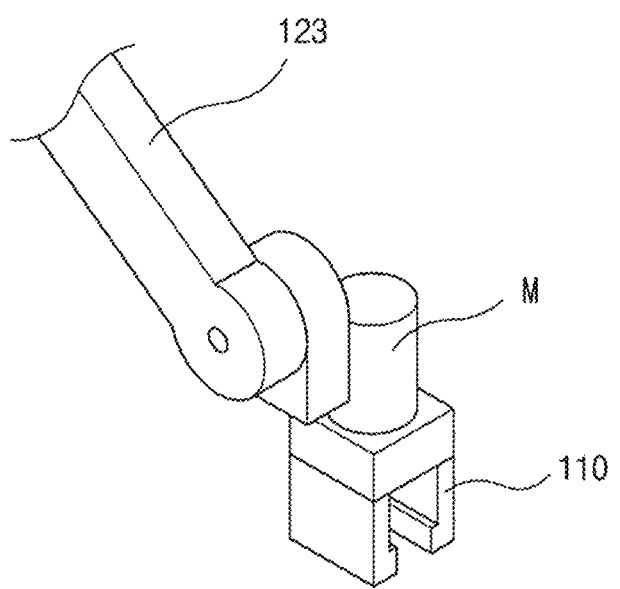

As shown in FIG. 6, a fourth embodiment of the picking arm 100 is characteristic in that the gripper 110 is provided with a motor that is axially oriented so that the gripper 110 can axially rotate. As such, if the gripper 110 can axially rotate, the angle at which the gripper 110 is oriented to pick up food can be easily adjusted, thus enhancing the applicability of the gripper 110.

The feeding arm 200 is provided with the spoon 210 onto which the food that is picked up by the picking arm 100 is placed. The feeding arm 200 functions to transfer the spoon 210 to the mouth of the user. Here, because the feeding arm 200 has only to transfer the food that has been placed on the spoon 210 by the picking arm 100 to the mount of the user, the feeding arm 200 may have only a single degree of freedom.

The feeding arm 200 should be able to maintain the spoon 210 provided on the end thereof horizontal while transferring food in the spoon 210 to the mouth of the user.

Figure 7:
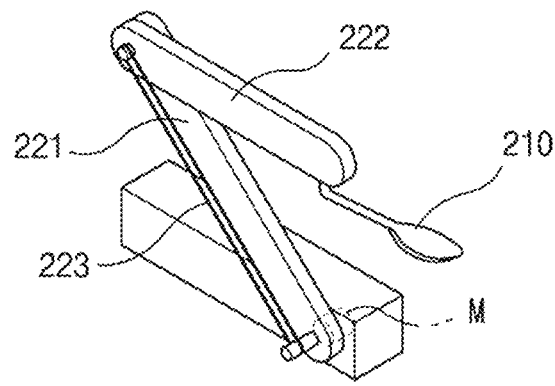
FIGS. 7 through 10 illustrate embodiments of a feeding arm which is one of the elements constituting the present invention.

As shown in FIG. 7, a first embodiment of the feeding arm 200 includes a first link 221 which is connected at a first end thereof to a motor so that the first link 221 can vertically swing around a rotating shaft, and a second link 222 which is rotatably connected to a second end of the first link 221 by a hinge. The hinge is connected to the motor provided on the first link 221 by a belt 223 so that the second link 222 can vertically swing in conjunction with the first link 221. The spoon 210 is provided on an end of the second link 222 and oriented horizontally with the second link 222.

In the first embodiment, the first link 221 and second link 222 are moved in conjunction with each other by the belt 223, thus facilitating maintaining the spoon 210 horizontal. Furthermore, because the number of motors can be reduced, the structure of the apparatus can be simple.

Figure 8:
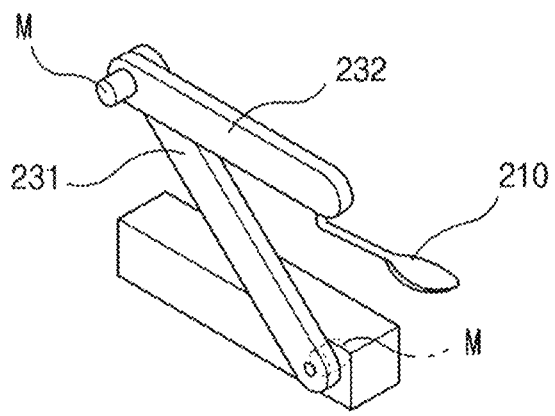

As shown in FIG. 8, a second embodiment of the feeding arm 200 includes a first link 231 which is connected at a first end thereof to a motor so that the first link 231 can vertically swing around a rotating shaft, and a second link 232 which is hinged to a second end of the first link 231 and is able to be vertically swung by rotation of a motor. The spoon 210 is provided on an end of the second link 232 and oriented horizontally with the second link 232.

In the second embodiment, every joint is provided with the motor so that the power of the feeding arm 200 is increased, thus reducing the possibility of malfunction, and more easily and smoothly producing the operation of the feeding arm 200. Furthermore, unlike the first embodiment, the second embodiment has no belt on the first link 231. This makes it possible to adjust the length of the first link 231. For example, a prismatic joint or the like may be applied to the first link 231 so that the length of the first link 231 can be adjusted. In this case, the first link 231 can be used in such a way that when the present invention is used, it is extended, and when the present invention is stored, it can be contracted, thus making it more convenient to use.

Figure 9:
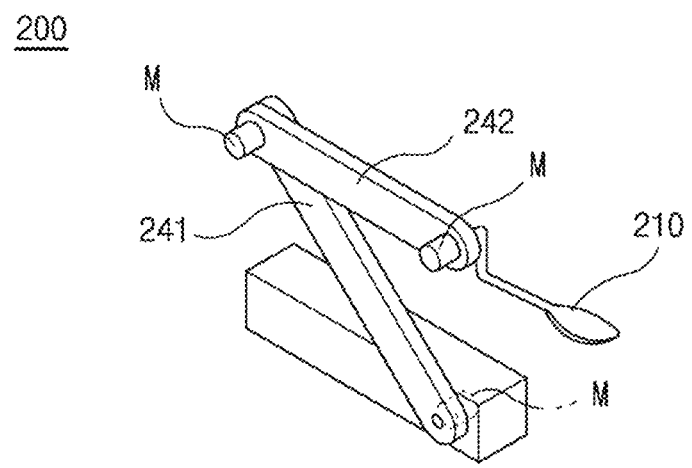

As shown in FIG. 9, a third embodiment of the feeding arm 200 includes a first link 241 which is connected at a first end thereof to a motor so that the first link 241 can vertically swing around a rotating shaft, and a second link 242 which is hinged to a second end of the first link 241 and is able to be vertically swung by rotation of a motor, wherein the spoon 210 is hinged to an end of the second link 242 so that the spoon 210 can be vertically swung by rotation of a motor.

Unlike the second embodiment, the third embodiment includes an additional motor which makes it possible to adjust the angle of the spoon 210 with respect to the vertical direction. In this embodiment that can adjust the angle of the spoon 210, the three motors are generally used to operate the feeding arm 200 and transfer the spoon 210 to the mouth of the user in such a way that not only the position of the spoon 210 but also the angle thereof is adjusted. Therefore, the spoon 210 can move more precisely and smoothly.

Figure 10:
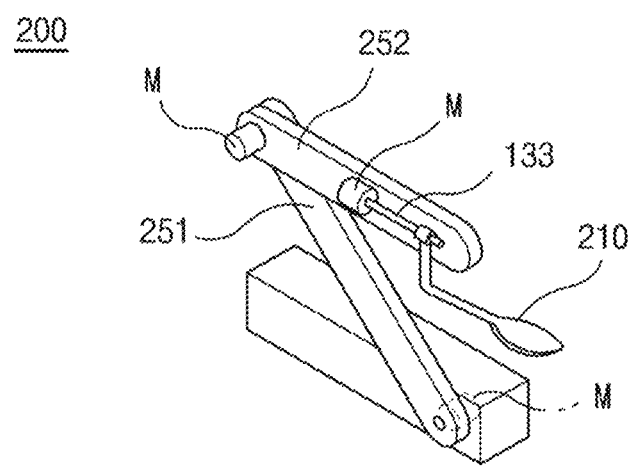

As shown in FIG. 10, a fourth embodiment of the feeding arm 200 includes a first link 251 which is connected at a first end thereof to a motor so that the first link 251 can vertically swing around a rotating shaft, and a second link 252 which is hinged to a second end of the first link 251 and is able to be vertically swung by rotation of a motor, wherein the spoon 210 is connected to an end of the second link 242 by a prismatic joint 133 so that the spoon 210 can horizontally move.

In the fourth embodiment, the spoon 210 can horizontally move, thus making it convenient for the user to control the spoon 210, and facilitating transferring food in the spoon 210 without spilling. In this embodiment, the prismatic joint 133 can be used in the same manner as those of the other embodiments.

Preferably, a sensing means 500 is provided on at least either the picking arm 100 or the feeding arm 200. In other words, even though a patient or the elderly and infirm can eat food by himself/herself using the present invention, it is preferable that he/she must be continuously monitored or be able to easily sound an alarm, because an emergency can occur anytime.

Different kinds of means, such as a camera or a motion sensor, can be used as the sensing means 500, so long as it can monitor the patient or the elderly and infirm.

Furthermore, it is preferable for the picking arm 100 and the feeding arm 200 to be provided in a single frame 600. The reason for this is that because the picking arm 100 and the feeding arm 200 make a pair and are used together, installing them in a single frame 600 can make it convenient to use. More preferably, the picking arm 100 and the feeding arm 200 can move along rails (not shown) provided on the frame 600 so that the relative positions therebetween can be adjusted, thus making it more convenient to use in response to conditions of the user.

In addition, the picking arm 100 and the feeding arm 200 may be separately provided and directly installed on the corners of the table. Therefore, the above-mentioned structure in which the arms are provided in the single frame 600 is not essential.

The input device 300 is used for the user to control the picking arm 100 and the feeding arm 200. The input device 300 is connected to the picking arm 100 and the feeding arm 200 by a wire-wireless device.

The input device 300 is a general manipulation means which is manipulated by the hand of the user to control the picking arm 100 and the feeding arm 200. The input device 300 may be a mechanical device such as a joystick, and any means can be used.

Furthermore, if the feeding assistant robot is generally automated, manipulating only a single button of the input device 300 may make it possible for the user to have a meal. This must be systemized and previously set by the control unit (not shown) which will be described herein below. This automated system is more suitable for a patient or the elderly and infirm who is not able to easily move his/her arms. This will be explained in detail after the description of the control unit (not shown).

The control unit (not shown) is electrically connected to the picking arm 100, the feeding arm 200, and the input device 300. The control unit controls the operation of the picking arm 100 and the feeding arm 200 in accordance with the instruction of the input device 300.

A typical PC may be used as the control unit (not shown). Alternatively, the control unit may be of another type using a circuit device.

In the present invention, the control unit (not shown) controls the operation of the picking arm 100 and the feeding arm 200 depending on the manipulation of the input device 300. As stated above, the control unit may be configured such that the arms are individually and mechanically controlled or, alternatively, the entire apparatus may be systemized so that the overall process can be conducted by manipulating a single button Although the former can be embodied in such a way that the picking arm 100 and the feeding arm 200 are controlled by individual manipulation units, in the latter case, the overall operation of the apparatus must be set in the control unit (not shown).

In other words, there may be different sizes of food trays 10, and users have different body sizes. Therefore, such measurements must be previously set in the control unit so that the apparatus can pick up food at a correct position and supply food to a precise location.

For this, the prevent invention is configured such that it is operated in the following manner: the size and structure of the food tray 10 are previously input in the control unit (not shown); and when the user designates food disposed at a predetermined position using the input device 300, the picking arm 100 automatically moves to the corresponding food, the gripper 110 picks up the food and places it on the spoon 210 of the feeding arm 200, and then the feeding arm 200 moves the spoon 210 to the mouth of the user.

Moreover, the present invention is characterized in that the user may designate several kinds of foods disposed at different positions at one time. That is, according to the user, he/she may separately eat different kinds of foods, or eat them together, for example, in such a way that side dishes are placed on steamed rice. For this, the present invention is configured such that the user can designate several food sections 11 containing different kinds of foods to eat at one time. In other words, the control unit (not shown) controls the apparatus such that when the user designates several food sections 11, the picking arm 100 successively transfers pieces of food contained in the designated food sections 11 to the feeding arm 200, and after the selected foods have been transferred to the feeding arm 200, the feeding arm 200 transfers the food to the mouth of the user.

As shown in FIG. 11, the input device 300 may comprise a touchpad LCD. In this case, the LCD displays the shape of the food tray 10 as it is. If the user only touches a portion of the LCD that corresponds to the position of selected food contained in the food tray, the picking arm 100 and the feeding arm 200 are automatically operated so that the selected food can be put into the mouth of the user.

Alternatively, as shown in FIG. 12, the input device 300 may be of a simple button type. In this case, the user memorizes marks corresponding to respective sections of the food tray. The control unit (not shown) is set such that when the user pushes a button corresponding to a selected mark, corresponding food is automatically transferred to the mouth of the user.

Moreover, the automated system may be configured such that, when the user designates food disposed at a predetermined position using the input device 300, the control unit (not shown) instructs the gripper 110 of the picking arm 100 to be immersed in a water bottle and pulled out of it before the gripper 110 picks up the food. Thanks to this, when the gripper 110 picks up food such as steamed rice which is sticky and places onto the spoon 210, the food can be prevented from sticking to the gripper 110.

Furthermore, as shown in FIGS. 13 through 15, the automated system may be configured such that each food section is partitioned into several areas of appropriate sizes depending on the size of the gripper 110, and the gripper 110 picks up pieces of food in the order named. The reason for this is that because the user cannot individually designate the positions of pieces of food in each food section 11 in the automated system, it is preferable for the user to preset the order along which he/she can eat all pieces of food in each food section 11.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

The invention claimed is:

1. A feeding assistant robot, comprising:
    a picking arm provided with a gripper picking up food placed on a top surface of a food tray;
    a feeding arm provided with a spoon onto which the food picked up by the picking arm is placed, the feeding arm transferring the spoon to a mouth of a user; and
    an input device enabling the user to instruct the picking arm and the feeding arm to be operated,
    wherein the picking arm includes a link connected at a first end thereof to a motor so that the link horizontally rotates around a rotating shaft,
    wherein the gripper is provided on a second end of the link so as to be vertically movable, and
    wherein, after gripping the food, the gripper moves upwardly so that the food is lifted up by the gripper to be apart from the top surface of the food tray.

2. The feeding assistant robot according to claim 1, wherein the link comprises:
    a first link connected at a first end thereof to the motor, the first link being horizontally rotatable around the rotating shaft by said motor; and
    a second link hinged to a second end of the first link so that the second link is horizontally rotated around the second end of the first link by rotation of a second motor,
    wherein the gripper is provided on an end of the second link so as to be vertically movable relative to said end of the second link.

3. The feeding assistant robot according to claim 2, wherein the gripper is connected to the second link by a prismatic joint so as to be vertically movable.

4. The feeding assistant robot according to claim 1, wherein the feeding arm comprises:
    a first link connected at a first end thereof to a motor so that the first link is able to vertically swing around a rotating shaft; and
    a second link hinged to a second end of the first link, the second link being able to be vertically swung by rotation of a motor,
    wherein the spoon is provided on an end of the second link and oriented horizontally with the second link.

5. The feeding assistant robot according to claim 1, wherein the feeding arm comprises:
    a first link connected at a first end thereof to a motor so that the first link is able to vertically swing around a rotating shaft; and
    a second link hinged to a second end of the first link, the second link being able to be vertically swung by rotation of a motor,
    wherein the spoon is hinged to an end of the second link and is able to be vertically swung by rotation of a motor.

6. The feeding assistant robot according to claim 1, wherein the feeding arm comprises:
    a first link connected at a first end thereof to a motor so that the first link is able to vertically swing around a rotating shaft; and
    a second link hinged to a second end of the first link, the second link being able to be vertically swung by rotation of a motor,
    wherein the spoon is connected to an end of the second link by a prismatic joint so as to be horizontally movable.

7. The feeding assistant robot according to claim 1, wherein each of food sections of the food tray is partitioned into a plurality of areas depending on a size of the gripper, wherein the gripper picks up pieces of food in the food section in a preset sequence.

8. The feeding assistant robot according to claim 1, wherein the picking arm and the feeding arm are provided in a single frame.

* * * * *